US012731697B2

(12) United States Patent
Nonaka et al.

(10) Patent No.: US 12,731,697 B2
(45) Date of Patent: Sep. 8, 2026

(54) MEDICAL PROCEDURE PREPARATION GUIDE APPARATUS, MEDICAL PROCEDURE PREPARATION GUIDE METHOD, NON-TRANSITORY RECORDING MEDIUM RECORDING MEDICAL PROCEDURE PREPARATION GUIDE PROGRAM

(71) Applicant: OLYMPUS MEDICAL SYSTEMS CORP., Tokyo (JP)

(72) Inventors: Osamu Nonaka, Sagamihara (JP); Masahiro Ashizuka, Hino (JP); Takeo Suzuki, Kawagoe (JP)

(73) Assignee: Olympus Medical Systems Corp., Tokyo (JP)

(*) Notice: Subject to any disclaimer, the term of this patent is extended or adjusted under 35 U.S.C. 154(b) by 89 days.

(21) Appl. No.: 18/748,240

(22) Filed: Jun. 20, 2024

(65) Prior Publication Data

US 2024/0428957 A1 Dec. 26, 2024

Related U.S. Application Data

(60) Provisional application No. 63/522,741, filed on Jun. 23, 2023.

(51) Int. Cl.
*G16H 70/20* (2018.01)

(52) U.S. Cl.
CPC .................................. *G16H 70/20* (2018.01)

(58) Field of Classification Search
CPC ........ G16H 70/20; G16H 30/20; G16H 30/40; G16H 40/20
See application file for complete search history.

(56) References Cited

U.S. PATENT DOCUMENTS

2019/0206576 A1* 7/2019 Shelton, IV ........... G16H 40/63

FOREIGN PATENT DOCUMENTS

JP 2004-323135 A 11/2004

OTHER PUBLICATIONS

Taaffe K, Ferrand YB, Khoshkenar A, Fredendall L, San D, Rosopa P, Joseph A. Operating room design using agent-based simulation to reduce room obstructions. Health Care Manag Sci. Jun. 2023;26(2):261-278. doi: 10.1007/s10729-022-09622-3. Epub Dec. 19, 2022. PMID: 36529790; PMCID: PMC10369668. (Year: 2022).*

(Continued)

*Primary Examiner* — Joshua B Blanchette
(74) *Attorney, Agent, or Firm* — Morgan, Lewis & Bockius LLP

(57) ABSTRACT

A medical procedure preparation guide apparatus includes one or more processors comprising hardware, wherein the one or more processors configured to: acquires an examination type which is a type of examination or treatment using medical equipment; searches a database for layout information about candidate equipment corresponding to the examination type, where the database stores layout information about spaces necessary for the examination or the treatment in relation to a plurality of sets of the medical equipment necessary for the examination or the treatment; and outputs the layout information about the candidate equipment including dynamic human body measurements information about a person concerned with the examination or the treatment using the medical equipment.

20 Claims, 11 Drawing Sheets

(56) References Cited

OTHER PUBLICATIONS

Human Integration Design Handbook (HIDH), NASA, Jun. 5, 2014, Available At https://www.nasa.gov/wp-content/uploads/2015/03/human_integration_design_handbook_revision_1.pdf; Select Pages (Year: 2014).*

* cited by examiner

Figure 3:
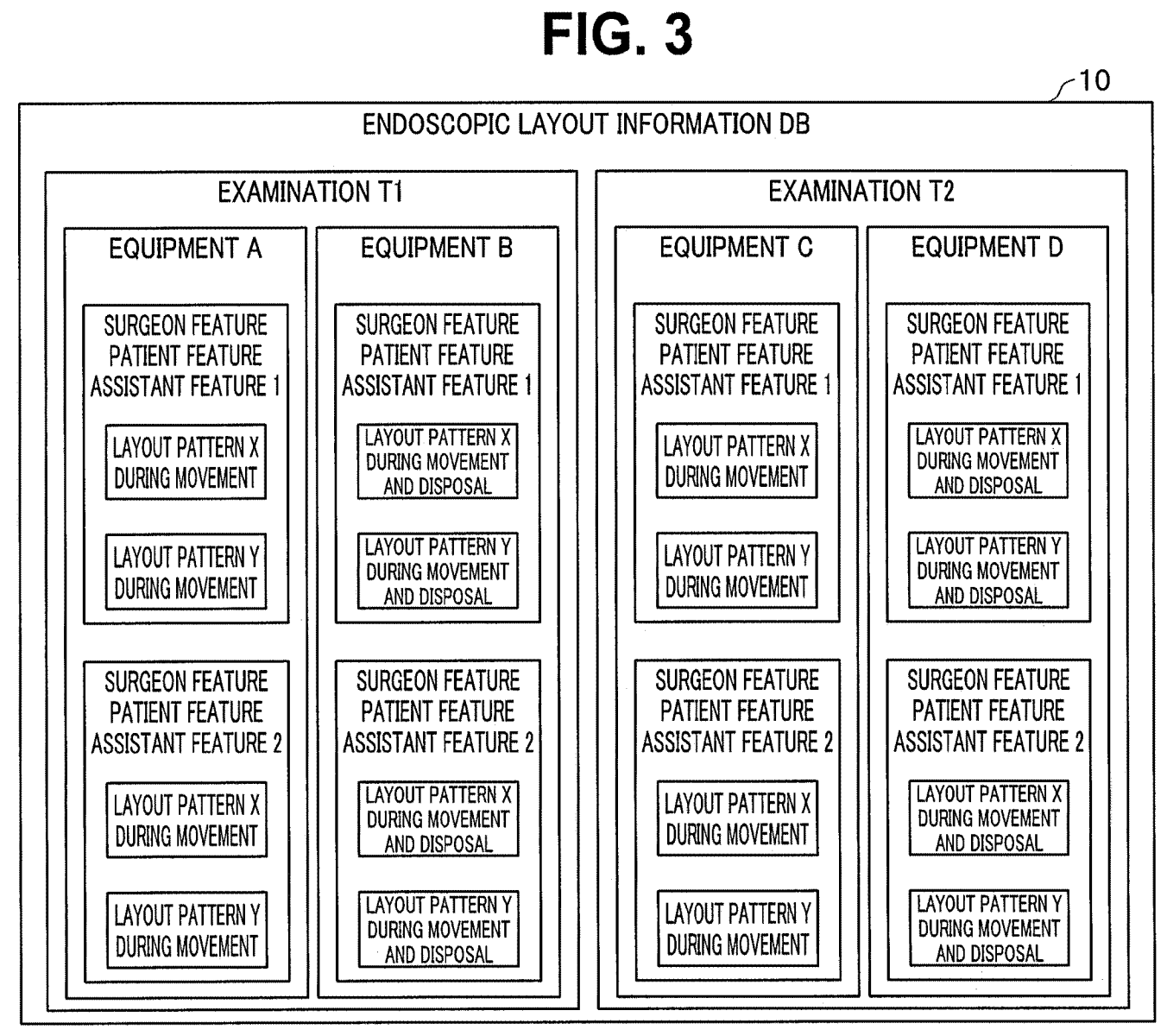

ENDOSCOPIC LAYOUT INFORMATION DB

EXAMINATION T1

EQUIPMENT A

SURGEON FEATURE
PATIENT FEATURE
ASSISTANT FEATURE 1

LAYOUT PATTERN X DURING MOVEMENT

LAYOUT PATTERN Y DURING MOVEMENT

SURGEON FEATURE
PATIENT FEATURE
ASSISTANT FEATURE 2

LAYOUT PATTERN X DURING MOVEMENT

LAYOUT PATTERN Y DURING MOVEMENT

EQUIPMENT B

SURGEON FEATURE
PATIENT FEATURE
ASSISTANT FEATURE 1

LAYOUT PATTERN X DURING MOVEMENT AND DISPOSAL

LAYOUT PATTERN Y DURING MOVEMENT AND DISPOSAL

SURGEON FEATURE
PATIENT FEATURE
ASSISTANT FEATURE 2

LAYOUT PATTERN X DURING MOVEMENT AND DISPOSAL

LAYOUT PATTERN Y DURING MOVEMENT AND DISPOSAL

EXAMINATION T2

EQUIPMENT C

SURGEON FEATURE
PATIENT FEATURE
ASSISTANT FEATURE 1

LAYOUT PATTERN X DURING MOVEMENT

LAYOUT PATTERN Y DURING MOVEMENT

SURGEON FEATURE
PATIENT FEATURE
ASSISTANT FEATURE 2

LAYOUT PATTERN X DURING MOVEMENT

LAYOUT PATTERN Y DURING MOVEMENT

EQUIPMENT D

SURGEON FEATURE
PATIENT FEATURE
ASSISTANT FEATURE 1

LAYOUT PATTERN X DURING MOVEMENT AND DISPOSAL

LAYOUT PATTERN Y DURING MOVEMENT AND DISPOSAL

SURGEON FEATURE
PATIENT FEATURE
ASSISTANT FEATURE 2

LAYOUT PATTERN X DURING MOVEMENT AND DISPOSAL

LAYOUT PATTERN Y DURING MOVEMENT AND DISPOSAL

FIG. 11

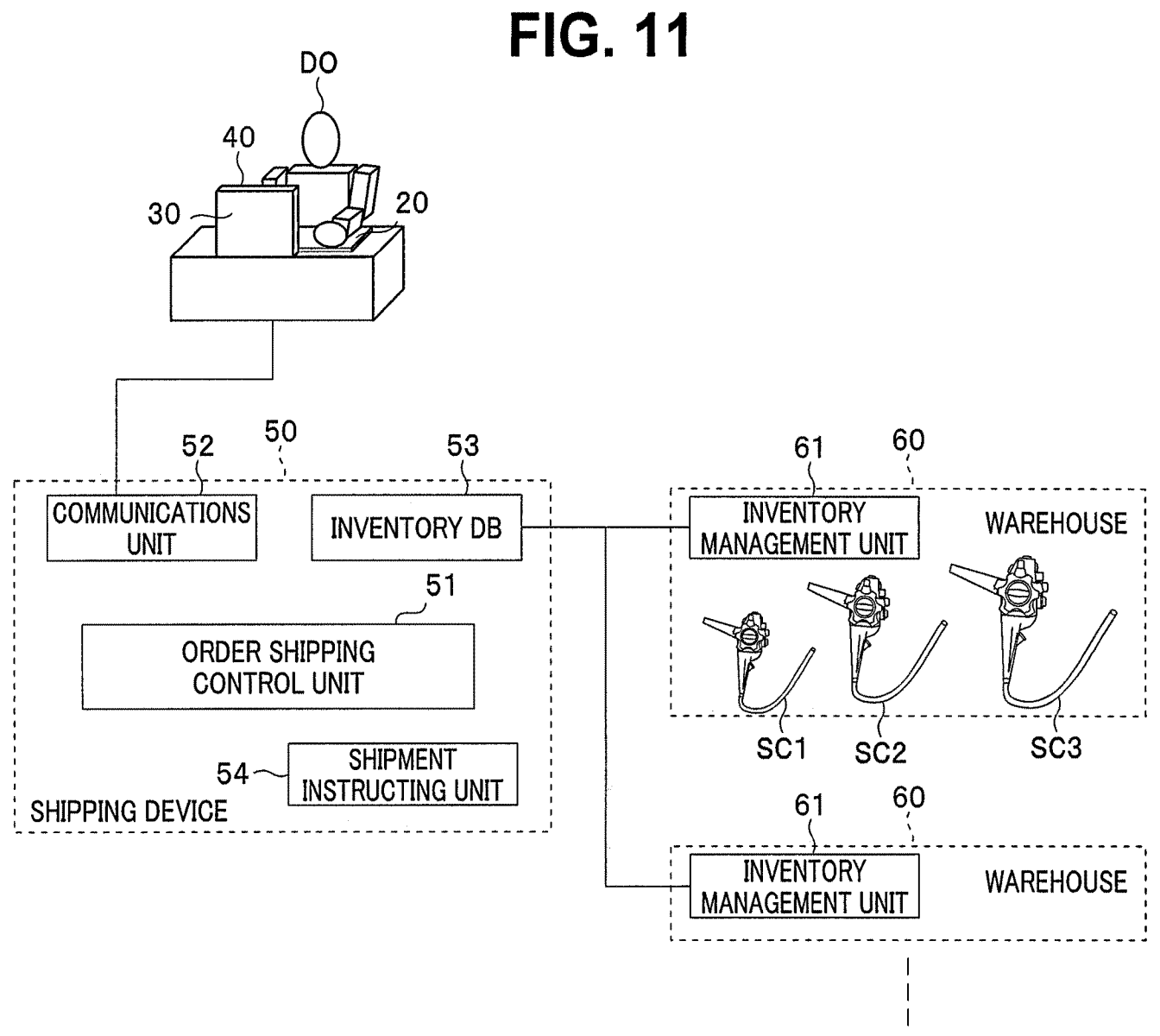

DO
20
40
30
50
52
COMMUNICATIONS UNIT
53
INVENTORY DB
51
ORDER SHIPPING CONTROL UNIT
54
SHIPMENT INSTRUCTING UNIT
SHIPPING DEVICE
60
61
INVENTORY MANAGEMENT UNIT
WAREHOUSE
SC1
SC2
SC3
60
61
INVENTORY MANAGEMENT UNIT
WAREHOUSE

MEDICAL PROCEDURE PREPARATION GUIDE APPARATUS, MEDICAL PROCEDURE PREPARATION GUIDE METHOD, NON-TRANSITORY RECORDING MEDIUM RECORDING MEDICAL PROCEDURE PREPARATION GUIDE PROGRAM

RELATED APPLICATION DATA

This application is based on and claims priority under 35 U.S.C. § 119 to U.S. Provisional Application No. 63/522,741, filed on Jun. 23, 2023, the entire contents of which are incorporated herein by reference.

BACKGROUND

Technical Field

The present disclosure relates to a medical procedure preparation guide apparatus, a medical procedure preparation guide method, a non-transitory recording medium recording a medical procedure preparation guide program.

Description of Related Art

Conventionally, regarding various medical examinations in medical institutions, for reasons such as large size of medical equipment and the need for cleaning facilities, it has often been the case that an examination room is provided for each examination and a subject moves to the examination room to get examined. Recently, however, in connection with downsizing of medical equipment and elimination of the need for juxtaposition of cleaning facilities due to increases in single-use instruments, there have been increasing cases in which there is no need to conduct examinations in specific examination rooms and there have been cases in which examinations are conducted by moving medical equipment to a location desired by the subject. This saves the subject the labor of moving and makes it easy to create an environment in which it is easy to undergo examinations.

SUMMARY

According to one aspect of the present disclosure, there is provided a medical procedure preparation guide apparatus that includes one or more processors comprising hardware, wherein the one or more processors being configured to: acquire an examination type which is a type of examination or treatment using medical equipment; search a database for layout information about candidate equipment corresponding to the examination type, where the database stores layout information about spaces necessary for the examination or the treatment in relation to a plurality of sets of the medical equipment necessary for the examination or the treatment; and output the layout information about the candidate equipment including dynamic human body measurements information about a person concerned with the examination or the treatment using the medical equipment.

According to one aspect of the present disclosure, there is provided a medical procedure preparation guide method that includes: acquiring an examination type which is a type of examination or treatment using medical equipment; searching a database for layout information about candidate equipment corresponding to the examination type, where the database stores layout information about spaces necessary for the examination or the treatment in relation to a plurality of sets of the medical equipment necessary for the examination or the treatment; and outputting the layout information about the candidate equipment including dynamic human body measurements information about a person concerned with the examination or the treatment using the medical equipment.

According to one aspect of the present disclosure, there is provided a non-transitory recording medium recording a medical procedure preparation guide program, wherein the program causes a computer to execute procedures for: acquiring an examination type which is a type of examination or treatment using medical equipment; searching a database for layout information about candidate equipment corresponding to the examination type, where the database stores layout information about spaces necessary for the examination or the treatment in relation to a plurality of sets of the medical equipment necessary for the examination or the treatment; and outputting the layout information about the candidate equipment including dynamic human body measurements information about a person concerned with the examination or the treatment using the medical equipment.

According to one aspect of the present disclosure according to the first aspect, there is provided the layout information is stored in the database by including the dynamic human body measurements information.

According to one aspect of the present disclosure according to the first aspect, the one or more processors being configured to output information about a result of comparison between information that indicates a spatial layout of an expected layout space in which the medical equipment is placed and the layout information that includes the dynamic human body measurements information.

According to one aspect of the present disclosure according to the first aspect, the layout information includes information about a space for use to carry in the medical equipment and a space for use to house the medical equipment.

BRIEF DESCRIPTION OF THE DRAWINGS

FIG. 3 is an explanatory diagram for illustrating endoscopic layout information.

FIG. 9 is an explanatory diagram showing an example of a carry-in simulation display assuming that medical equipment is carried in.

FIG. 11 is a block diagram showing a second embodiment.

DETAILED DESCRIPTION

Figure 1:
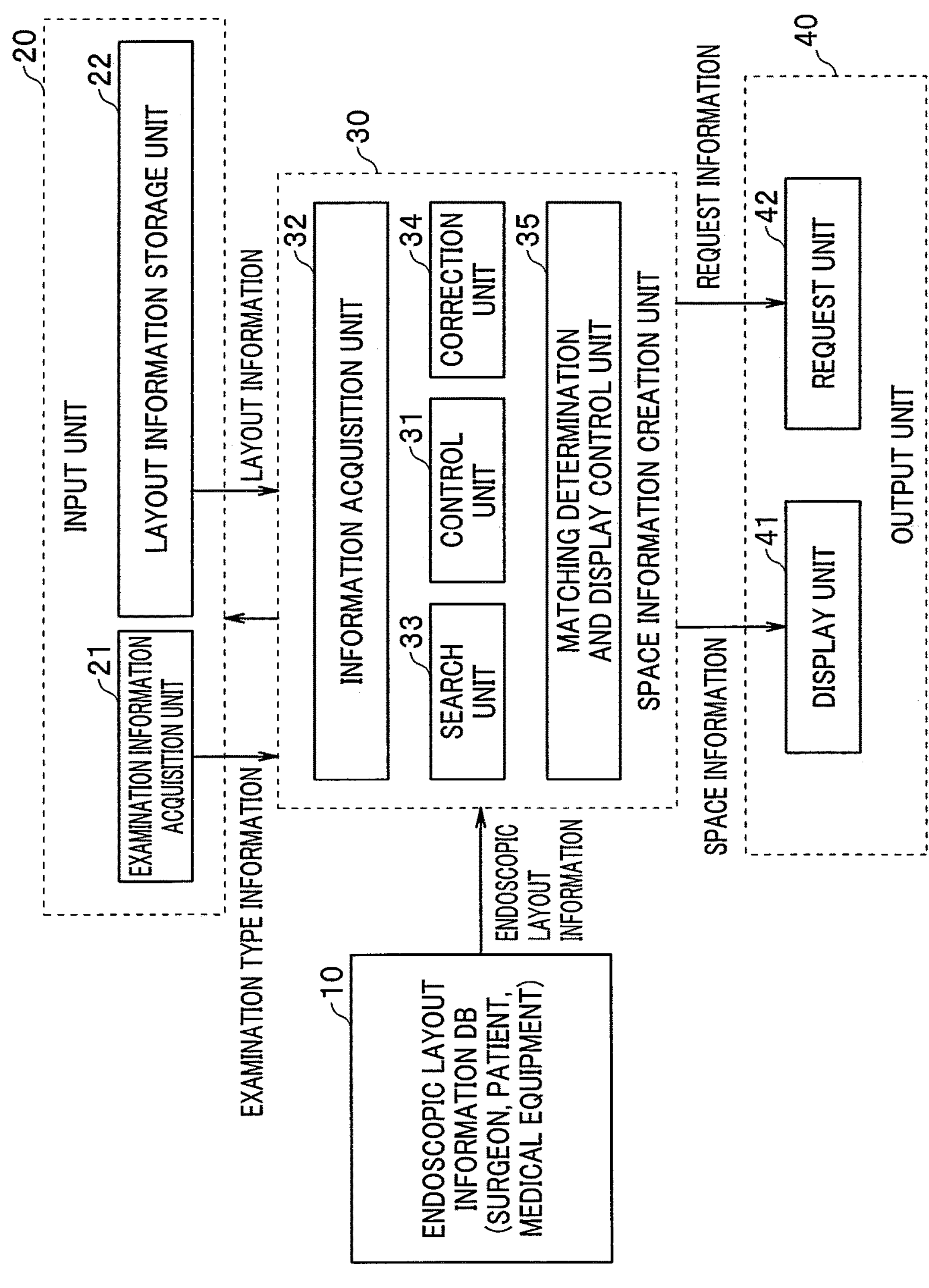
FIG. 1 is a block diagram showing a medical procedure preparation guide apparatus according to a first embodiment of the present disclosure.

Conventionally, it has generally been the case that endoscopic examinations are conducted in well-equipped hospitals. However, the situation is such that concentration of patients on large hospitals causes concern about problems such as waiting time and burnout of medical workers. Due to recent downsizing of medical equipment, medical equipment that has conventionally been able to be installed only in large hospitals is now available in small and medium clinics, and the small and medium clinics are expected to conduct examinations conventionally conducted in large hospitals. Furthermore, depending on details of examinations, the examinations can be conducted by carrying medical equipment into the homes of patients.

Under such circumstances, equipment sales and services adaptable to various medical examination/treatment spaces are expected and medical equipment sales and services whereby medical equipment is merely installed in special rooms as is conventionally the case are insufficient. In other words, it is important to provide services that allow medical workers who conduct examinations in a relevant room or space to check what kind of examination is possible in an existing typical hospital room or medical examination/treatment space not prepared for a special examination.

However, it is not easy to determine what kind of medical equipment can be used among a wide variety of medical equipment in an actual examination environment. It is necessary to take into consideration installation space of the medical equipment, difficulty of carry-in, operating environment of the medical equipment, and the like and it is extremely difficult to select the most suitable examination equipment and facilities that will allow appropriate examinations to be conducted in places convenient to subjects.

In other words, there is demand for a technique that will allow medical workers to check usable medical equipment in advance, i.e., before examination facilities or equipment are carried in, purchased, rented, or the like. If a technique for such prior checking is provided, the most suitable examination equipment and facilities can be selected, allowing appropriate examinations to be conducted in places convenient to subjects. Alternatively, in a situation such as when sufficient space is not available in an anticipated place, prior adjustments can be made such that examinations can be conducted by moving to another place.

Note that Japanese Patent Application Laid-Open Publication No. 2004-323135 discloses a technique for searching a living space for free space for goods based on map information about the living space. However, the proposal does not present results of a layout created for the free space including movable ranges of tools and persons, and even if the proposal is used, it is not easy to determine whether medical workers can perform a medical procedure appropriately in desired places.

Embodiments of the present disclosure will be described in detail below with reference to the drawings.

First Embodiment

FIG. 1 is a block diagram showing a medical procedure preparation guide apparatus according to a first embodiment of the present disclosure. The present embodiment makes a proposal about selection and arrangement of medical equipment according to a layout and the like of a placement location where the medical equipment is placed and thereby effectively supports preparation for medical procedures such as examinations, treatment, or the like. Note that medical equipment herein means an aggregate of one or more equipment items used to achieve a predetermined medical procedure. Whereas in the present embodiment, description is given of an example of supporting preparation for endoscopic examinations using medical equipment including an endoscope as medical equipment, the medical equipment does not necessarily have to include an endoscope, and the present disclosure is applicable not only to endoscopic examinations, but also to an apparatus that supports preparation for various types of medical procedure such as various types of examination and various types of treatment.

Whereas the term "medical procedure" is used here, in examining an object using the apparatus, because the present disclosure is also applicable to a technique used when the object does not correspond to a medical procedure, the present disclosure is also applicable to an apparatus that supports preparation for various types of examining action such as various types of examination and various types of treatment.

In FIG. 1, the medical procedure preparation guide apparatus includes an input unit 20, a space information creation unit 30, and an output unit 40. The medical procedure preparation guide apparatus accesses an endoscopic layout information DB (database) 10 and thereby acquires endoscopic layout information. Note that the endoscopic layout information DB 10 may be provided on the medical procedure preparation guide apparatus.

The endoscopic layout information DB 10 may be created by photographing, with a camera or the like, how corresponding medical equipment is actually used, analyzing resulting images (or a motion video), and calculating or estimating a required space for each set of equipment. In that case, a technique adopted may involve determining positions of the medical equipment and photographic equipment in advance, adopting a standard photographic method, and thereby allowing photographic information to be converted into space information. Alternatively, a technique may be adopted that converts the background into a special image, thereby making it easy to separate the medical equipment and the medical workers concerned. Alternatively, a technique may be adopted that involves attaching special tags to the medical equipment and hands or bodies of the medical workers, thereby making it easy to determine time variation in relative location and movement between equipment items and the bodies, using photographic images.

A technique called motion capture and used to animate CG characters, analyze motion of athletes, control robots or drones in real time may be adopted, where the motion capture is a technique for converting movements of persons or things into digital data. Recently, being known as "generative AI," a machine learning technique for automatically generating an output from sample data has been spreading. The technique may be adopted to create the endoscopic layout information DB 10.

In other words, the medical procedure preparation guide apparatus may create the database by calculating and estimating dimensions of an expected layout space and each member in the expected layout space based on images obtained by photographing the expected layout space in advance. Many medical institutions photograph how various medical examinations and treatments are carried out and introduce resulting images on websites and the like, and the database can be created with reference to such images. First, as long as medical equipment is photographed with the model identified, a reference size can be seen, positions and sizes of the photographed medical workers as well as a range (which can be estimated from arm lengths and the like) needed for work can be estimated based on the reference size. Of course, information necessary for the database may be designed to be obtained by accepting as input such images, causing an inference model to be trained using teacher data annotated with necessary spaces, and thereby obtaining images. Even if there is not a database, space information may be presented by calculating or estimating the information. In that case, the database may no longer an essential element of the present disclosure. In that case, the medical procedure preparation guide apparatus according to the present disclosure accepts as input a photographic image taken when specific medical equipment is used, and outputs layout information about spaces necessary for the examination or the like using the medical equipment, based on an inference model trained using teacher data annotated with a necessary space in using the specific medical equipment.

The endoscopic layout information DB 10 stores information about the medical equipment used in performing a predetermined medical procedure, i.e., endoscopic layout information classified by type of examination or treatment (type of medical procedure). The endoscopic layout information makes it possible to grasp a space needed to achieve a medical procedure performed using medical equipment. Examples of the endoscopic layout information include not only information such as a name, model number, and shape that identify medical equipment, but also information about the size of medical equipment, information used to place one or more pieces of medical equipment needed in order to perform a medical procedure in a conceivable space (hereinafter referred to as the expected layout space), and information about a working space needed in order to perform a medical procedure such as examinations using medical equipment. As the expected layout space, any of various types of space, big or small, is adopted including a room in small and medium clinics, the home of a patient, and an examination room in a ward of a large hospital. For example, it is sufficient that the expected layout space is a space where the medical equipment can be used regardless of the originally intended use of the space, and various types of space are conceivable including outdoor tents and evacuation facilities where a medical procedure is performed. The endoscopic layout information may contain not only character or numeric information, but also image information.

In other words, the "endoscopic layout information" can be rephrased as required-space information (about a space in and around an installation space of an endoscopy apparatus) that expresses user's operating/working position and motion range (including a margin) with respect to the apparatus as two-dimensional or three-dimensional sizes together with an area occupied by the apparatus, where user's operating/working position and motion range have been estimated at the time of design of the endoscopy apparatus. Alternatively, the endoscopic layout information may be expressed as information about the space required by the apparatus and the user (or two-dimensional range information corresponding to spreading directions of a floor and substituting the information about the space), where the information is obtained by monitoring time variation in positional relationship and movements of the apparatus and user not only at the time of design, but also during actual operation of the apparatus for verification.

Because the disclosure is not limited to endoscopes, the endoscopic layout information may be rephrased as "examination-related layout information" or more simply as "layout information." This corresponds to a sum of an area necessary for installation of the apparatus (including a relevant device group), a space domain, and a floor area that requires the space domain, with operator's dynamic human body measurements (described below) taken into account. However, the positional relationship between the apparatus and the operator depends on ability and preferences of the operator, and it is advisable to allow some margin for that.

Note that according to the present embodiment, the endoscopic layout information includes information about the medical equipment placed during endoscopy, but may include information about medical equipment placed not only during endoscopy, but also during a medical procedure, such as ultrasound endoscopy, respiratory system examinations, and various types of treatment, performed using various types of medical equipment. In the following description, the types of examination or treatment will be referred to simply as the examination type for simplicity of description. In other words, the endoscopic layout information is classified by examination type.

The endoscopic layout information also includes human body measurements information about a surgeon, assistants, and the like who perform a medical procedure as well as human body measurements information about a patient. Note that as the endoscopic layout information, dynamic human body measurements are adopted, where the dynamic human body measurements are dimensions needed for motions and movements performed during a medical procedure and are dimensions of a space resulting from a combination of persons and things. Alternatively, as the endoscopic layout information, static human body measurements, which are dimensions of human bodies themselves, may be adopted.

The "dynamic human body measurements" are determined based on human body measurements, which are dimensions of various parts of a human body such as height, and correspond to a spatial range needed for trifling motions performed by human bodies to stand up or sit down, or raise or lower hands, for apparatus/equipment-based work, or for an examination of an object by the apparatus/equipment-based work, or to dimensions within which the human bodies can move. By considering the dynamic human body measurements, size and width of the space are set such that the space will be easy to use and easy for the human bodies to act in. Size and range information needed for preparation and clearing-up may be taken into consideration.

To conduct an examination using an endoscope, the surgeon inserts the endoscope into the human body by operating the endoscope with both hands. To insert the endoscope into the upper or lower digestive tract, the surgeon needs to insert the endoscope by conforming to the shape of the digestive tract, and the surgeon inserts the endoscope using not only the hands, but also twisting of the body and the like. Therefore, during endoscopy, the motion of the surgeon is larger than during a medical procedure using other medical equipment and much space is needed in order to enable movement of the surgeon. For this reason, the dynamic human body measurements information is included in the endoscopic layout information. Note that the dynamic human body measurements may vary with the way and the like of a medical procedure.

Note that the endoscopic layout information can be expressed by an equipment layout that shows an arrangement of medical equipment and the like in a predetermined space (hereinafter referred to as an equipment space) taken up for medical equipment and operation of the medical equipment.

Figure 2:
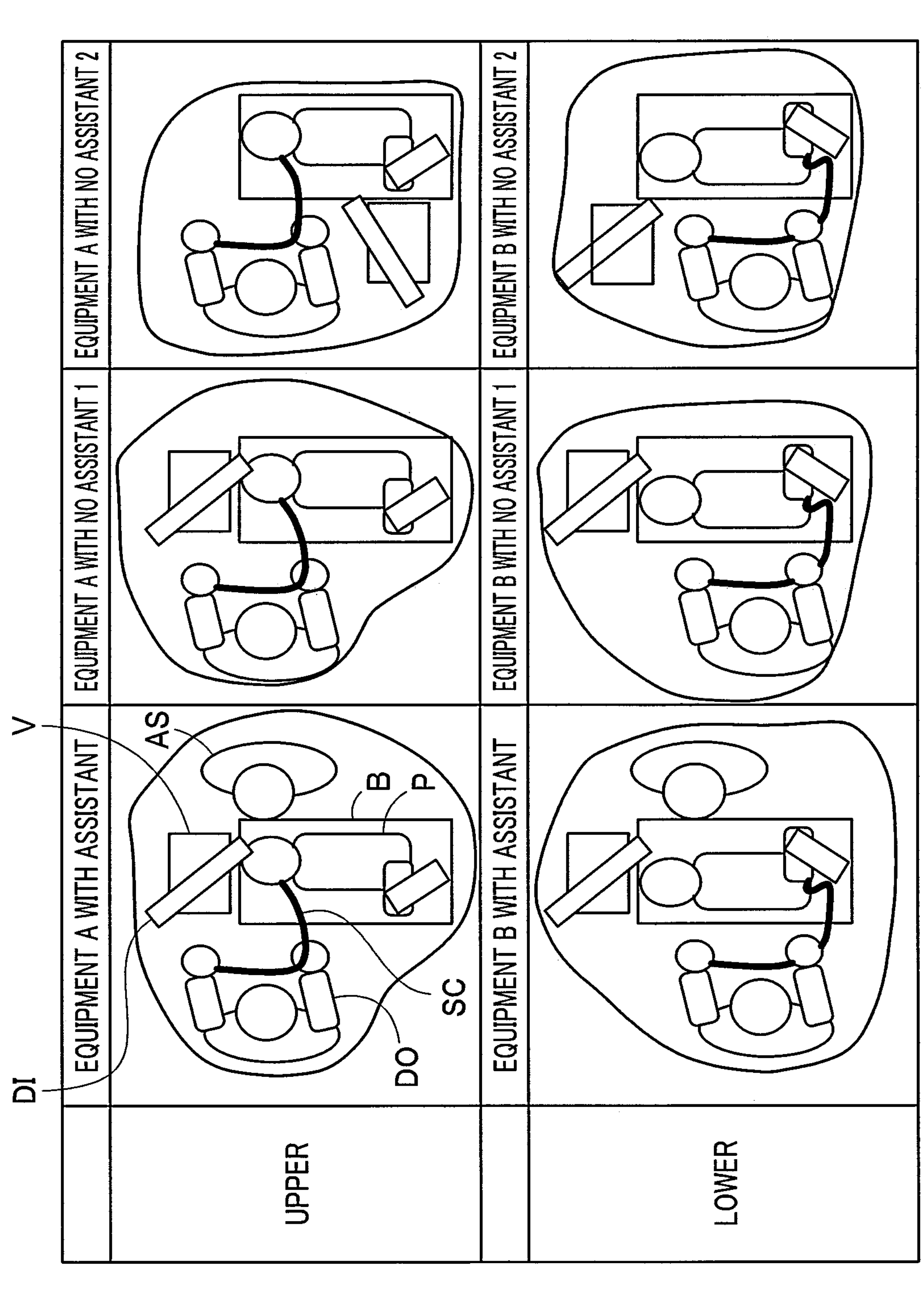
FIG. 2 is an explanatory diagram for illustrating endoscopic layout information.

FIGS. 2 and 3 are explanatory diagrams for illustrating endoscopic layout information. FIG. 2 shows an example in which in relation to upper digestive tract (upper) endoscopy and lower digestive tract (lower) endoscopy, the endoscopic layout information registered in the endoscopic layout information DB 10 is represented by image information. In the example of FIG. 2, in relation to the upper digestive tract endoscopy, the endoscopic layout information about medical equipment A is registered in the endoscopic layout information DB 10, and in relation to the lower digestive tract endoscopy, the endoscopic layout information about medical equipment B is registered in the endoscopic layout information DB 10.

The endoscopic layout information in FIG. 2 shows a layout example (recommended layout) containing medical equipment A, medical equipment B, a surgeon DO, an assistant AS, and a patient P. In other words, each recommended layout includes dynamic human body measurements information. Note that medical equipment A and medical equipment B include an endoscope SC, a video processor V, a stand on which the video processor V is placed, a display DI, and a bed BE. Note that a frame surrounding medical equipment A, medical equipment B, the surgeon DO, the assistant AS, the patient P, and the like shows an equipment space and roughly indicates a space needed as an expected layout space.

Endoscopy is simply divided into upper endoscopy and lower endoscopy and an example of using the endoscopy in medical checkups is shown here. However, there are examinations specialized in special symptoms such as accidental ingestion or a stomachache. In that case, positions of the examination equipment or surgeon, the number of assistants, or the like may change, but such cases are not illustrated for simplicity of explanation.

In the example of FIG. 2, endoscopic layout information has been registered in the endoscopic layout information DB 10, showing three layout examples of medical equipment A: a layout example in which medical equipment A, a surgeon DO, and an assistant AS are placed when an assistant AS is needed; and two layout examples in which medical equipment A and a surgeon DO are placed when no assistant AS is needed. Endoscopic layout information has also been registered in the endoscopic layout information DB 10, showing three layout examples of medical equipment B: a layout example in which medical equipment B, a surgeon DO, and an assistant AS are placed when an assistant AS is needed; and two layout examples in which medical equipment B and a surgeon DO are placed when no assistant AS is needed. As illustrated in FIG. 2, the endoscopic layout information may be important as two-dimensional information such as a map or a room layout diagram for making it possible to display the shape and dimensions of the space required to occupy the floor. For example, if the equipment space has coordinate information (including scale information) corresponding to the outer circumference of the required space, it is possible to intuitively compare whether the horizontal projection area of the equipment and the work space fits with respect to the floor area of a specific space such as a clinic examination room or the empty space area of the floor. In addition, the endoscopic layout information may include the equipment space and the dynamic human body measurements, which are determined by the dimensions of the equipment (in terms of floor area), and the dynamic human body measurements are a space determined by the standard human body dimensions (height, width when both hands are extended to the left and right, etc.). There may be no difference in the equipment space between the person who handles the device if it is the same device, but the dynamic human body measurements change depending on the human body dimensions of the person using the device, so when correcting for endoscopic layout information, the equipment space and the dynamic human body divide into measurements and make corrections for the dynamic human body measurements. The information recorded in the endoscopic layout information DB 10 is stored so that these can be separated, and only one of them may be corrected (enlarged or reduced) to form endoscopic layout information together with the equipment space.

Although it has been stated that the endoscopic layout information stored in the endoscopic layout information DB 10 is information about spaces that allow a medical procedure to be performed, the endoscopic layout information may further include information about a storage space of medical equipment (storage space information) and/or information about carry-in of medical equipment (carry-in space information). Furthermore, the endoscopic layout information may include information about power supply, a wet area, and the like needed in order to perform a medical procedure. FIG. 2 shows an arrangement example when there is only one assistant, but an arrangement in which a plurality of assistants are arranged may be stored as the endoscopic layout information.

Whereas the equipment space, the storage space, and the carry-in space, and the like are represented here by layout information by being seen in a simplified manner as planes spreading in a horizontal direction on the floor, the spaces may include information in a height direction from the floor, or three-dimensional space information containing plane space information in the horizontal direction at each height level.

Whereas it has been stated that the endoscopic layout information is classified by examination type, the endoscopic layout information may be further subdivided according to dynamic human body measurements.

FIG. 3 illustrates by example contents of the endoscopic layout information corresponding to two types of endoscopic examinations T1 and T2, where the information is registered in the endoscopic layout information DB 10. In the example of FIG. 3, the endoscopic layout information DB 10 stores endoscopic layout information about equipment A and equipment B in relation to examination T1 and endoscopic layout information about equipment C and equipment D in relation to examination T2. The example of FIG. 3 shows a case in which two pieces each of endoscopic layout information is stored in relation to each set of equipment A to D. The endoscopic layout information in relation to equipment A and equipment C contains information about the space involved during movement and endoscopy regarding layout pattern X and contains information about the space involved during movement and endoscopy regarding layout pattern Y. Meanwhile, the endoscopic layout information in relation to equipment B and equipment D contains information about the space involved during movement, endoscopy, and disposal regarding layout pattern X and contains information about the space involved during movement, endoscopy, and disposal regarding layout pattern Y. Each piece of the endoscopic layout information includes a surgeon feature, a patient feature, and an assistant feature regarding dynamic human body measurements, and in the example of FIG. 3, endoscopic layout information differing in the assistant feature is stored for different sets of equipment. The endoscopic layout information DB 10 organizes data so that medical professionals can select medical devices for which they may not have some knowledge based on information such as what kind of examination they want to do, which is the needs of medical professionals. In addition, for each specific test, a plurality of devices that can be selected by a medical professional can be presented, so that the medical professional can select the one that is easy to use. Furthermore, in addition to the endoscopic layout information, the endoscopic layout information DB 10 may also store specifications such as the functions and performance of each medical device. For example, information such as touch operation or input method information, performance, function, and required external device may be provided. Since the method of operating the medical device may not necessarily uniform and may vary depending on the preference of the operator, information on the preference of the operator may be stored in the endoscopic layout information DB 10 together with the endoscopic layout information. By memorizing the specifications of each medical device, medical professionals can select a device while referring to information such as specifications stored in the endoscopic layout information DB, and there may be no confusion in the actual state of use. For example, in the case of an endoscope, where the movement and posture of the operator's hands such as a doctor are important in the operation of the device, endoscopic layout information that also takes into account the posture and the range of motion of the limbs may be important. The endoscopic layout information DB 10 includes not only the layout information but also information on the assumed position of the operator and the space necessary for equipment operation. FIGS. 2 and 3 shows that the endoscopic layout information is arranged so that it can be changed according to the characteristics of the operator. In addition, since there is also an element of the characteristics of the subject (height, body shape, and preferred body position may be different), the endoscopic layout information DB is configured so that information corresponding to the projected area is included as an equipment space so that it can be taken into account.

Figure 4:
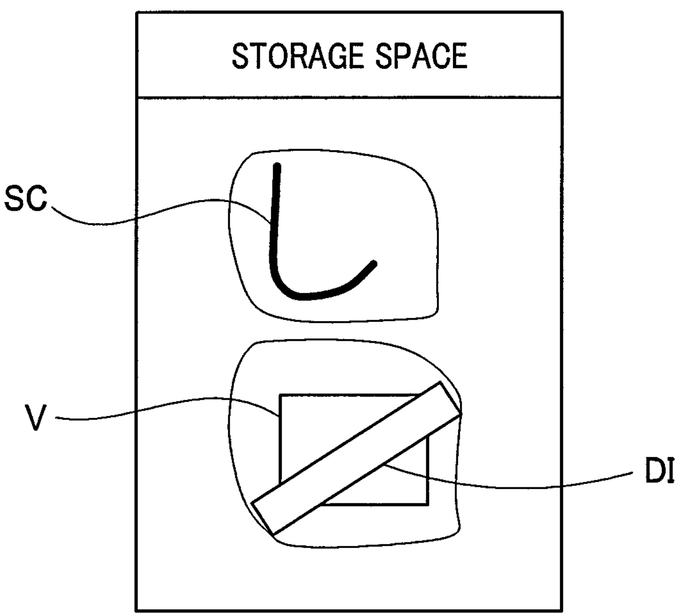
FIG. 4 is an explanatory diagram for illustrating storage space information.

FIG. 4 is an explanatory diagram for illustrating storage space information. The storage space is not a space needed during a medical procedure performed using medical equipment, but is a space needed in order to store medical equipment that does not need an operator's space. Note that the storage space needed for an endoscope apparatus may vary before and after use, and pre-use storage space information and post-use storage space information may be adopted as storage space information.

The example of FIG. 4 shows, by means of image information, an example of a storage space needed when the medical equipment is made up of the endoscope SC, the video processor V, and the display DI. Generally, the endoscope SC and the video processor V are separated. The video processor V and the display DI may be placed on a non-illustrated cart, and a storage space needed in such cases is roughly indicated by a frame in FIG. 4.

The storage space is a clean space before medical equipment is used, but after use, unlike before the use, the storage space is assumed to be a space that permits contamination after the use of the medical equipment and easily allows disposal and cleaning.

In FIG. 1, an input unit 20 includes an examination information acquisition unit 21 and a layout information storage unit 22. The examination information acquisition unit 21 acquires information about the type of examination (hereinafter referred to as examination type information), where the examination is a medical procedure. For example, the examination information acquisition unit 21 may include an operation section such as a non-illustrated keyboard or mouse and may be configured to allow the user to input the type of examination by operating the operation section. The examination information acquisition unit 21 outputs the acquired examination type information to the space information creation unit 30.

The layout information storage unit 22 holds spatial layout information about an expected layout space such as a room in a clinic where medical equipment is to be placed. Various members such as a desk, a chair, and a bed are placed in a room of a clinic or the like, and a free space for installation and the like of the medical equipment can be shown by a spatial layout that represents a layout state of individual members in the entire room of a clinic or the like. The layout information storage unit 22 outputs the spatial layout information to the space information creation unit 30. Note that the layout information storage unit 22 may hold the spatial layout information about the expected layout space in advance or calculate and hold spatial layout information based on image information about the expected layout space. For example, the expected layout space may be photographed with a smartphone or the like, with a resulting image being supplied to the layout information storage unit 22 such that the layout information storage unit 22 will calculate dimensions of various parts of the expected layout space from the image to obtain spatial layout information.

Whereas it has been stated above that the dynamic human body measurements information is contained in the endoscopic layout information stored in the endoscopic layout information DB 10, the human body measurements information about the surgeon, assistant, patient and the like may be set to be acquired through the input unit 20. For example, the human body measurements information may be inputted through the examination information acquisition unit 21 based on user operation or the human body measurements information may be set to be read from a server storing the human body measurements information in advance. Furthermore, the surgeon, the assistant, the patient, and the like may be photographed with a smartphone or the like, and the human body measurements may be calculated from a resulting image thereby to obtain the human body measurements information.

Note that regarding human body measurements and medical equipment sizes needed to install the medical equipment in the expected layout space in such a way as to allow a medical procedure to be performed, accurate values do not necessarily have to be used. For example, in the endoscopic layout information, medical equipment and human body measurements may be classified into standardized sizes such as large, medium, and small sizes. Regarding the spatial layout, sizes may be classified into standardized sizes such as large, medium, and small sizes or may be standardized into a standard layout of desks, beds, and the like. Regarding human body measurements for example, standard sizes may be stored as endoscopic layout information, and dynamic human body measurements may be corrected by a correction unit 34 described later according to actual sizes of the surgeon, patient, assistant, and the like. Such information can be calculated easily from information about angles of view of photographic equipment, distances during photography, size of an image pickup device, and the like.

The space information creation unit 30 includes a control unit 31, an information acquisition unit 32, a search unit 33, the correction unit 34, and a matching determination and display control unit 35. The control unit 31 exerts overall control over the input unit 20, the space information creation unit 30, and the output unit 40. Each component of the space information creation unit 30 may be made up of a processor that uses a CPU (central processing unit), an FPGA (field programmable gate array), or the like. Alternatively, each component of the space information creation unit 30 may control various parts by operating according to a program stored in a non-illustrated memory or may have all or part of functions implemented using hardware-based electronic circuitry.

The information acquisition unit 32 acquires endoscopic layout information from the endoscopic layout information DB 10. The information acquisition unit 32 also acquires examination type information from the examination information acquisition unit 21 and acquires spatial layout information from the layout information storage unit 22. The search unit 33 is given the examination type information acquired by the information acquisition unit 32, searches for endoscopic layout information corresponding to the examination type information, and selects one or more pieces of endoscopic layout information based on the examination type information. The retrieved endoscopic layout information indicates one or more candidates for the medical equipment to be placed in the expected layout space.

Note that when the endoscopic layout information is subdivided according to dynamic human body measurements and known dynamic human body measurements information about a surgeon or the like exists, the search unit 33 may search for information based on the examination type and dynamic human body measurements.

The control unit 31 may be set to give the endoscopic layout information acquired from the endoscopic layout information DB 10 to a display unit 41 (described later) as space information, causing the display unit 41 to display the endoscopic layout information. As described above, the endoscopic layout information makes it possible to grasp a space needed to perform a predetermined medical procedure. Moreover, the endoscopic layout information includes dynamic human body measurements information about a surgeon and the like. Therefore, as the control unit 31 presents a display based on the endoscopic layout information, the surgeon and the like can determine relatively easily whether an examination can be conducted by installing the medical equipment needed for the examination and the like to be conducted, in the expected layout space.

Furthermore, according to the present embodiment, to make such surgeon's determination easier, the matching determination and display control unit 35 is provided. The matching determination and display control unit 35 makes it easy to make a determination as to whether it is possible to perform a medical procedure by placing medical equipment in the expected layout space, based on the spatial layout information and the endoscopic layout information. For example, from the candidates for the medical equipment retrieved by the search unit 33, one set of medical equipment may be selected by being determined to be appropriate through user operation performed by the surgeon or the like. In that case, the matching determination and display control unit 35 may be set to generate display data for use to display models of the expected layout space and candidate medical equipment and output the display data to the output unit 40 as space information. Even if there is no user operation, when the layout information of the medical facility with a scale is present, the control unit 31 searches for and outputs a medical device that enters the empty space of the medical facility, and the display control unit 35 may generate display data for displaying the assumed space and the model of the medical device candidate. At this time, since there may be an examination room other than the assumed room, the user may be notified that there is another candidate medical device. For example, the endoscopic layout information DB 10 shown in FIG. 3 may be communicated via a communication unit (not shown) to search for necessary information according to the information organized in the endoscopic layout information. In this embodiment, the medical practitioner may narrow down the device suitable for simply entering the medical treatment that the medical professional wants to perform as a query. And even if there are a plurality of candidate devices, information such as specifications such as functions and performance of each device and the space required for installation and operation are organized for each device and can be retrieved from the endoscopic layout information DB 10. Healthcare professionals can easily select equipment based on this information (space information corresponding to the required floor projection area).

Recently, being known as "generative AI," a machine learning technique for automatically generating an output from sample data has been spreading. The technique may be used to generate display data.

The output unit 40 includes the display unit 41 and a request unit 42. The display unit 41, which can be made up of a display device such as an LCD, presents a display on a display screen based on display data from the space information creation unit 30.

Figure 5:
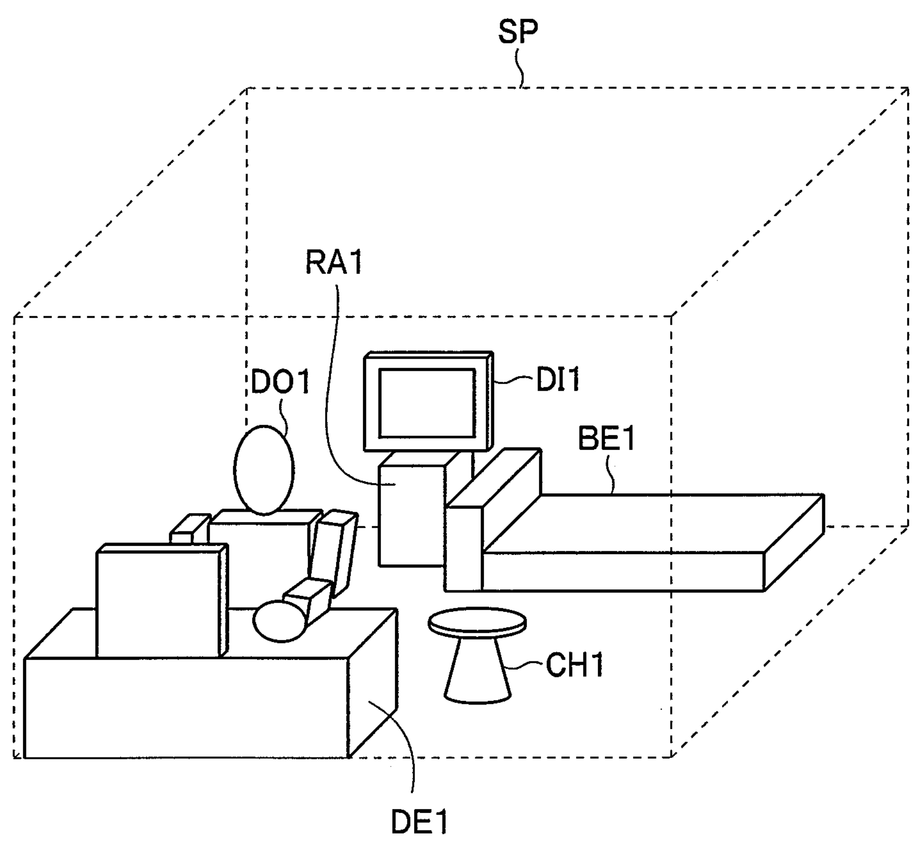
FIG. 5 is an explanatory diagram for illustrating selection of medical equipment made by a matching determination and display control unit 35.
Figure 6:
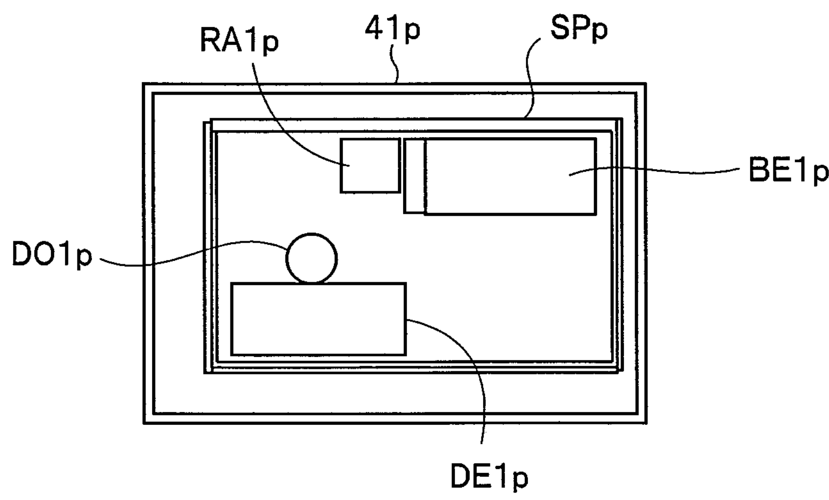
FIG. 6 is an explanatory diagram for illustrating selection of medical equipment made by the matching determination and display control unit 35.
Figure 7:
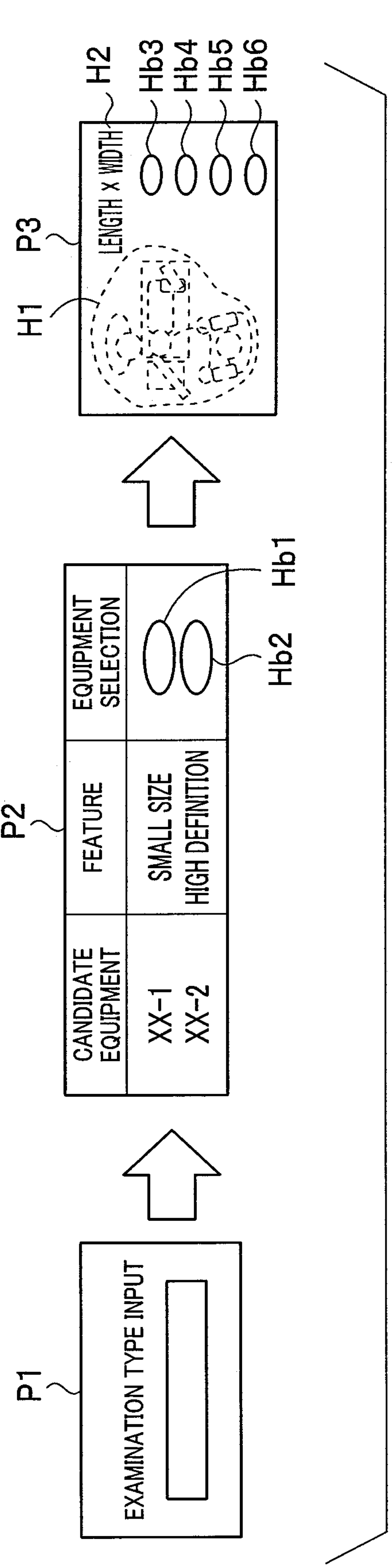
FIG. 7 is an explanatory diagram for illustrating selection of medical equipment made by the matching determination and display control unit 35.
Figure 8:
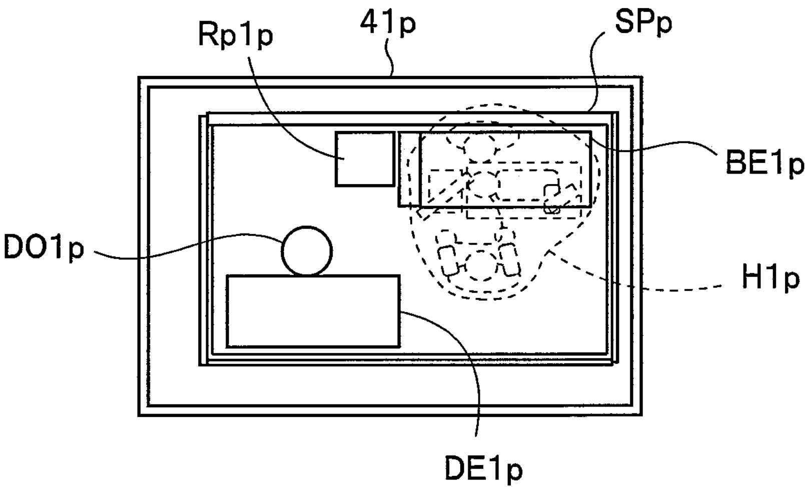
FIG. 8 is an explanatory diagram for illustrating selection of medical equipment made by the matching determination and display control unit 35.

FIGS. 5 to 8 are explanatory diagrams for illustrating selection of medical equipment made by the matching determination and display control unit 35. FIG. 5 shows a layout of an expected layout space SP in a room or the like of a clinic and FIGS. 6 and 8 show a display on a display screen 41*a* of the display unit 41. FIG. 7 shows an example of forms displayed by the control unit 31 and the matching determination and display control unit 35 to allow medical equipment to be selected by user operation.

There are a patient bed BE1, a stand RA1, a display DI1, a surgeon DO1, and a desk DE1 and a chair CHI in the expected layout space SP. It is assumed that the spatial layout information corresponding to the expected layout space SP contains, for example, information about the bed BE1, the stand RA1, the surgeon DO1, and the desk DE1. In this case, based on the spatial layout information, the matching determination and display control unit 35 can display an image SPp of the expected layout space SP including an image BE1*p* of the bed BE1, an image RA1*p* of the stand RA1, an image DO1*p* of the surgeon DO1, and an image DE1*p* of the desk DE1 on the display screen 41*a* as shown in FIG. 6.

The control unit 31 and the matching determination and display control unit 35 sequentially display the forms shown in FIG. 7. In other words, under the control of the control unit 31, the matching determination and display control unit 35 first displays an examination type input form P1. Through user's input operation with respect to the examination type input form P1, the examination information acquisition unit 21 acquires examination type information. The search unit 33 searches the endoscopic layout information DB 10 for endoscopic layout information corresponding to the examination type information to obtain candidates for the medical equipment corresponding to the examination type. The matching determination and display control unit 35 makes the display unit 41 display a selection form P2. The form P2 is used to display the retrieved candidates for the medical equipment, enabling user's selection operation.

The example of the selection form P2 in FIG. 7 shows that equipment XX-1 and equipment XX-2 have been retrieved as candidates for the medical equipment. Equipment XX-1 is distinguished by being a small-size endoscope apparatus. Equipment XX-2 is distinguished by being a high-definition endoscope apparatus. In the selection form P2, the matching determination and display control unit 35 displays selection buttons Hb1 and Hb2 for use to select equipment XX-1 and equipment XX-2, respectively. For example, when the user such as the surgeon performs a selection operation using the selection button Hb1, the matching determination and display control unit 35 outputs space information based on the endoscopic layout information about selected equipment XX-1 using a layout form P3. In the example of FIG. 7, as output of the space information, the matching determination and display control unit 35 makes the display unit 41 present equipment layout display H1, showing equipment layout of equipment XX-1.

Recently, being known as "generative AI," a machine learning technique for automatically generating an output from sample data has been spreading. Using the technique, information in the selection form P2 may be automatically generated from information in the examination type input form P1 as candidates, allowing the user to make a selection from among the candidates. The "generative AI" may also be used to generate information in the layout form P3 from the examination type input form P1 or to generate information in the layout form P3 from the selection form P2.

On websites and the like, various medical institutions introduce articles introducing how medical equipment is being used for patients and their families. On such websites, image information to be used to identify the type of medical equipment and information about layout of medical workers and a patient, for example, with reference to the medical equipment are recorded as an image. Thus, using such information as sample data, information can be created in the light of a matching determination site in the system.

In other words, a medical procedure preparation guide method according to the present application acquires an examination type of examination that uses medical equipment; acquires, as sample data, information to be used to identify a type of corresponding medical equipment from photographed images showing how the examination is using medical equipment introduced on websites and the like of a plurality of medical institutions, as well as information about layout of medical workers and a patient, for example, with reference to the medical equipment; generates layout information about spaces necessary for the examination in relation to the medical equipment necessary for the examination; and outputs the layout information including dynamic human body measurements information about a person concerned with examinations using the medical equipment.

The matching determination and display control unit 35 may present a display H2 having length and width sizes necessary for installation of the equipment XX-1 together with or instead of the equipment layout display H1. Furthermore, using the layout form P3, the matching determination and display control unit 35 may display a simulation button Hb3 for use to simulate placement of selected medical equipment in the expected layout space SP, a room information input button Hb4 for use to input spatial layout information corresponding to the expected layout space SP, a cancel button Hb5 for use to cancel a selection, and an order button Hb6 for use to order selected medical equipment.

In order to determine whether selected medical equipment can be placed in the expected layout space SP, spatial layout information about the expected layout space SP is needed. When spatial layout information has not been acquired by the information acquisition unit 32, when already acquired spatial layout information is changed, or when spatial layout information is obtained from images on a smartphone or the like, the room information input button Hb4 is used. When the room information input button Hb4 is operated, the control unit 31 creates spatial layout information using the layout information storage unit 22 and makes the information acquisition unit 32 acquire the spatial layout information.

When the simulation button Hb3 is operated, the matching determination and display control unit 35 presents a layout simulation display on the display unit 41, as output of space information when selected medical equipment is placed in the expected layout space SP. In this case, under the control of the control unit 31, the correction unit 34 brings the equipment layout display H1 and the image SPp of the expected layout space SP to the same scale based on the size of medical equipment according to the endoscopic layout information and sizes of various parts according to the spatial layout information about the expected layout space SP. Besides, as described above, if standard sizes are set as sizes of persons and medical equipment, the correction unit 34 corrects dynamic human body measurements according to information about body sizes of the surgeon, patient, assistant, and the like. The endoscopic layout information DB 10 organizes data so that medical professionals can select medical devices for which they do not have sufficient knowledge based on information such as what kind of examination they want to do, which is the needs of medical professionals. In addition, for each specific test, a plurality of devices that can be selected by a medical professional can be presented, so that the medical professional can select the one that is easy to use. Furthermore, in addition to the endoscopic layout information, the endoscopic layout information DB 10 may also store specifications such as the functions and performance of each medical device. For example, information such as touch operation or input method information, performance, function, and required external device may be provided. Since the method of operating the medical device is not necessarily uniform and may vary depending on the preference of the operator, information on the preference of the operator may be stored in the endoscopic layout information DB 10 together with the endoscopic layout information. By memorizing the specifications of each medical device, medical professionals can select a device while referring to information such as specifications stored in the endoscopic layout information DB, and there is no confusion in the actual state of use. For example, in the case of an endoscope, where the movement and posture of the operator's hands such as a doctor are important in the operation of the device, endoscopic layout information that also takes into account the posture and the range of motion of the limbs may be important. The endoscopic layout information DB 10 includes not only layout information but also information on the assumed position of the operator and the space necessary for equipment operation. In FIGS. 2 and 3, the figure shows that the endoscopic layout information is arranged so that it can be changed according to the characteristics of the operator. In addition, since there is also an element of the characteristics of the subject (height, body shape, and preferred body position may be different), the endoscopic layout information DB is configured so that information corresponding to the projected area is included as an equipment space so that it can be taken into account.

FIG. 8 shows an example of a layout simulation display. In FIG. 8, an image H1*p* corresponding to the equipment layout display H1 is displayed in superimposition on the image SPp of the expected layout space SP shown in FIG. 6. Note that the matching determination and display control unit 35 can change display position of the image H1*p* in response to user's mouse operation or the like with respect to the image H1*p*. The layout simulation display allows the user such as the surgeon to determine whether selected medical equipment can be placed in the room, whether a desired medical procedure can be performed using the medical equipment placed in the room, and so on. In the example of FIG. 8, it may be necessary to place the surgeon on one side of the bed BE1, and place the assistant on another side, and it can be seen that a medical procedure cannot be performed using the selected equipment XX-1 unless at least the bed BE1 is moved. The surgeon and the assistant can predict whether the medical procedure can be performed easily including whether the movement and the like can be carried out easily. It is assumed that the interior layout diagram in a medical facility has scale information, and the endoscopic layout information stored in the database, searched and read out is also two-dimensional shape information with scale information corresponding to the floor area, or coordinate information. By correcting the space information of the scale according to the scale of the indoor layout, matching the scale, and then displaying it on top of each other, it is possible to judge whether it fits in the empty space. If a medical professional can intuitively determine visually by looking at the display, and if each part of the layout diagram includes information on the wall and information that it is a desk, chair, or bed at the time of endoscopy, the control unit 30 may easily determine whether the space arranged at the time of endoscopy is stored in a space where they are not present (arrangement assumed space SP). In addition, assuming that the patient gets on the bed, in that case, if the endoscopic layout information DB10 is stored together with the space information at the time of examination having information indicating which part is the bed, the simulation image and the position of the bed in the clinic (The layout information has information that it is a bed, Pattern recognition and judgment may be made by artificial intelligence or the like) may be displayed superimposed as shown in FIG. 8. The space for examination and medical treatment has been described, but similarly, when transporting a medical device, if the layout information of the clinic or the other and the equipment space stored in the endoscopic layout information DB 10 both have scale information, it is possible to determine whether the space can be secured along the route of endoscope loading and unloading.

Note that the equipment layout display H1 shows a space in which the desired medical procedure can be performed. This is not only a space in which the medical equipment can be placed, but also a space in which the surgeon can perform the medical procedure, and moreover a space in which the medical procedure can be performed by allowing for movement lines of the surgeon and assistant. Thus, by placing the equipment layout display H1 in the image SPp within the expected layout space SP, the surgeon and the like can reliably determine whether the desired medical procedure can be performed.

Figure 9:
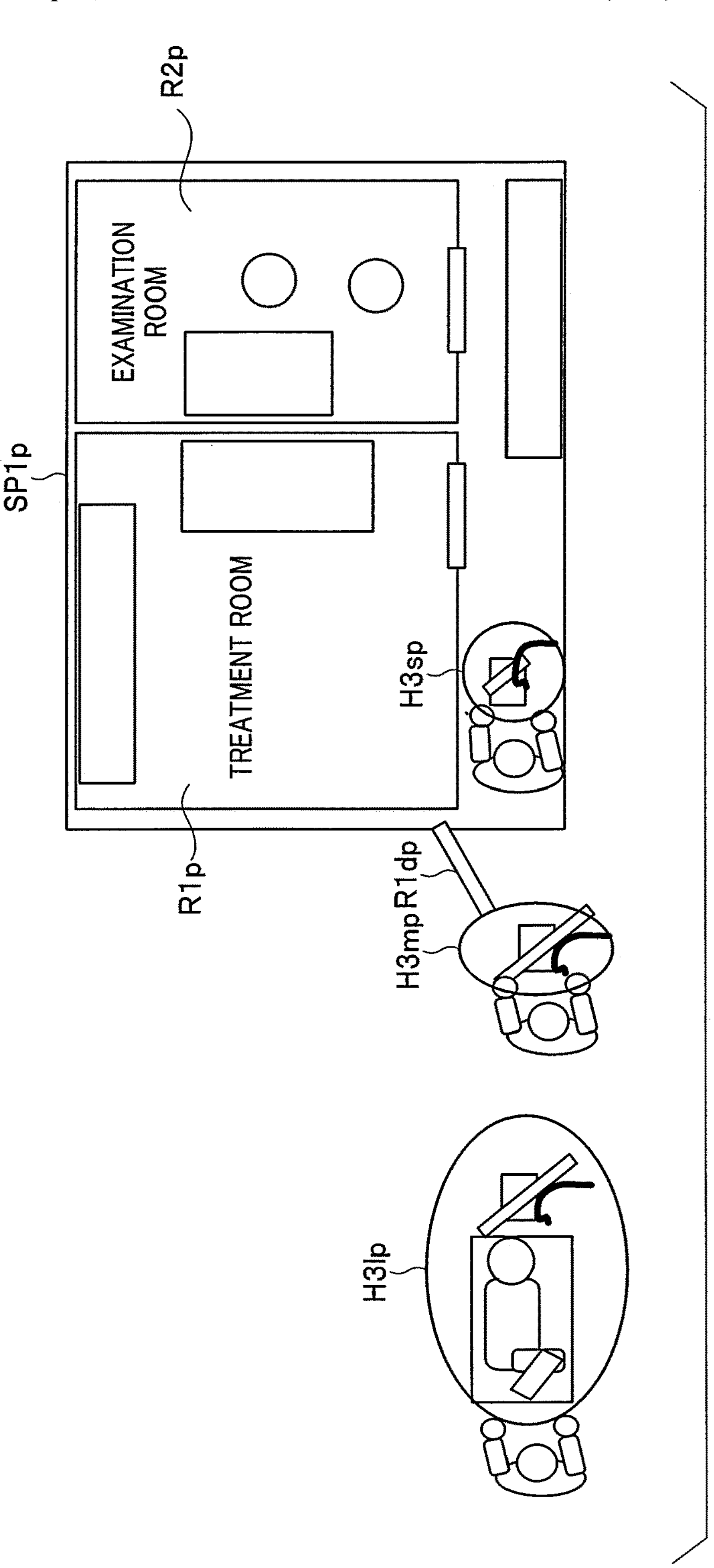

FIG. 9 is an explanatory diagram showing an example of a carry-in simulation display assuming that medical equipment is carried in.

The simulation button Hb3 in the layout form P3 of FIG. 7 is used to carry out a simulation to determine whether a medical procedure can be performed by placing medical equipment in the expected layout space SP, but a button for use to carry out a simulation to see whether selected medical equipment can be carried in may be provided. In the selection form P2, multiple sets of medical equipment can be selected simultaneously from multiple sets of candidate medical equipment. FIG. 9 shows an example in which multiple sets of medical equipment have been selected.

In the example of FIG. 9, three sets of candidate medical equipment differing in size have been selected and a carry-in simulation display is presented on the display screen 41*a*. An image SP1*p* of the expected layout space in FIG. 9 includes an image R1*p* of a treatment room and an image R2*p* of an examination room in the expected layout space having the treatment room and the examination room. The selected three sets of medical equipment are the largest medical equipment shown in an image H31*p*, medium medical equipment shown in an image H3*mp*, and the smallest medical equipment shown in an image H3*sp*.

Note that in the example of FIG. 9, the medical equipment to be carried in is placed on a cart. For example, not only an endoscope and a video processor, but also various types of medical equipment including vital management equipment such as an electrocardiograph are placed on the cart. The image H31*p* shows an example in which a patient lying on a bed is carried in together with medical equipment. Although not illustrated in FIG. 9, a space may be displayed by taking into consideration a layout of an assistant or nurse and movement lines of the assistant or nurse during carry-in or work.

To carry medical equipment into the treatment room, it may be necessary to pass the medical equipment through an entrance door and a corridor of the expected layout space. By comparing the size of an image R1*dp* of the entrance door and the size of a delivery destination such as the corridor with the images H31*p*, H3*mp*, H3*sp* of the respective sets of medical equipment, it can be seen that the medical equipment that can be carried in in the example of FIG. 9 is the smallest medical equipment shown in the image H3*sp*.

By referring to different simulation displays, the surgeon can relatively easily carry in and install the medical equipment in a desired space, and determine and select medical equipment that allows a desired medical procedure to be performed. If it is determined that the medical procedure cannot be performed using the selected medical equipment, the surgeon can make the selection form P2 displayed on the display unit 41 by pressing the cancel button Hb5 and select other medical equipment. On the other hand, if it is determined that the medical procedure can be performed using the selected medical equipment, the surgeon can order the selected medical equipment by pressing the order button Hb6. In that case, the control unit 31 places an order by giving information about the selected medical equipment to the request unit 42. The request unit 42, which includes a non-illustrated network interface, creates order information about the selected medical equipment and transmits the order information to a medical equipment maker or the like.

Figure 10:
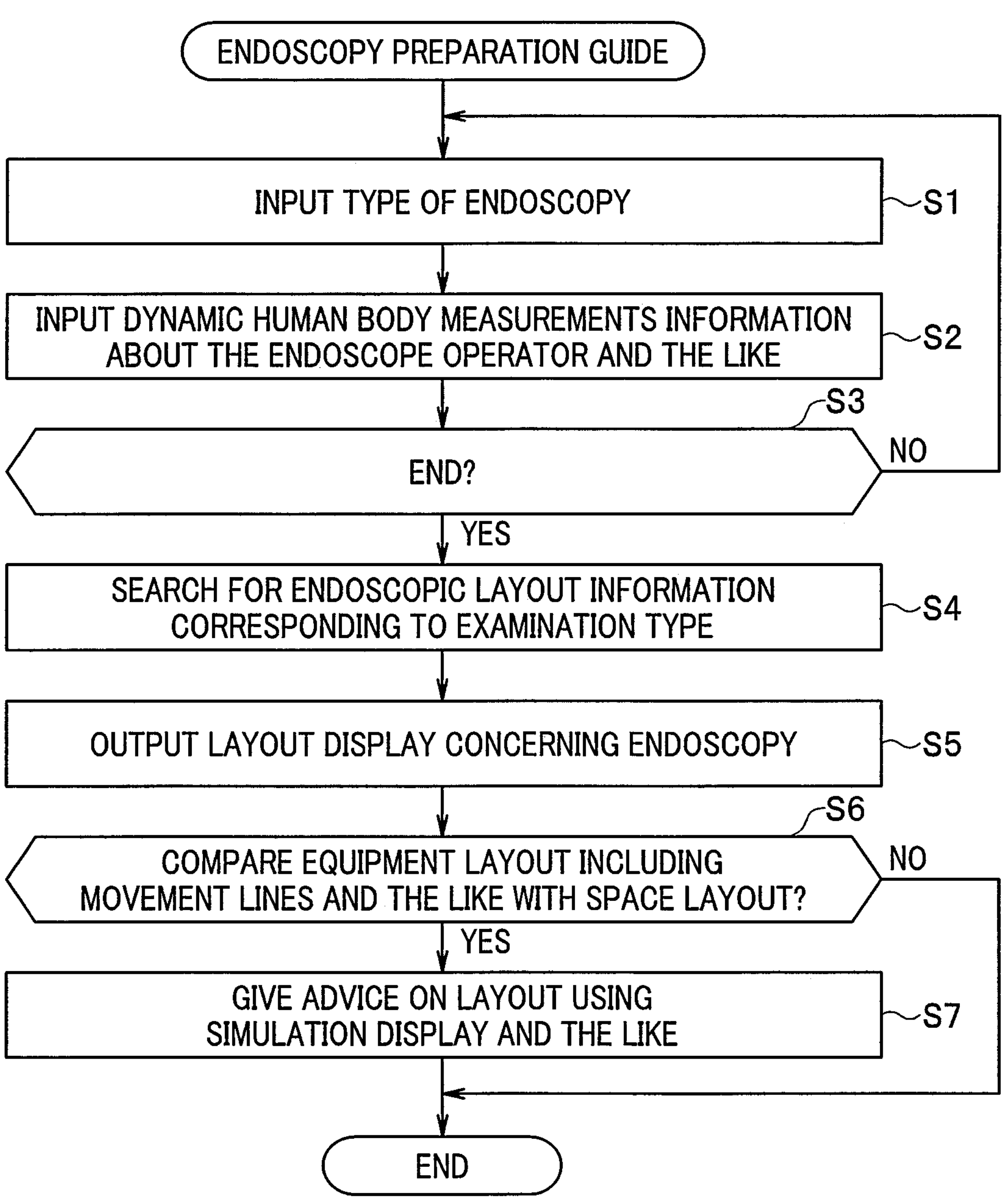
FIG. 10 is a flowchart for illustrating operation of the first embodiment.

Next, operation of the embodiment configured as described above will be described with reference to FIG. 10. FIG. 10 is a flowchart for illustrating operation of the first embodiment.

Many of small and medium clinics do not always keep facilities for endoscopy. Even in such a case, surgeons in such clinics sometimes want to conduct endoscopies. Recently, single-use endoscopes have been produced commercially, and it is assumed that a surgeon intends to carry endoscope apparatuses into the clinic and conduct endoscopies. In such a case, by operating a non-illustrated operation section and thereby displaying the examination type input form P1 of FIG. 7 on the display unit 41, the surgeon inputs an examination type in the input form P1 (S1 in FIG. 10).

If dynamic human body measurements information about an endoscope operator such as the surgeon is not contained in the endoscopic layout information stored in the endoscopic layout information DB 10, the examination information acquisition unit 21 acquires human body measurements information in S2. For example, dynamic human body measurements information is acquired based on user operation with respect to the non-illustrated operation section. The control unit 31 determines whether input operations in S1 and S2 are finished and carries out S1 and S2 until the input operations are finished. When the input operations in S1 and S2 are finished, the control unit 31 performs a search process using the search unit 33. Note that the operation flow in FIG. 10 is exemplary and dynamic human body measurements information may be set to be acquired before the process of S1 or after the search process of the search unit 33.

The search unit 33 searches the endoscopic layout information DB 10 for endoscopic layout information corresponding to the examination type (S4). Note that in this case, the search unit 33 may carry out the search using not only the examination type, but also information about dynamic human body measurements. In that case, medical equipment is searched for by taking into consideration the dynamic human body measurements of the surgeon and the like. Search results obtained by the search unit 33 is displayed, for example, as the selection form P2 of FIG. 7. The surgeon selects desired equipment from displayed candidates for medical equipment. In response to a selection operation performed by the surgeon or the like, the matching determination and display control unit 35 presents the equipment layout display that represents an equipment layout used during endoscopy, for example, as the layout form P3 of FIG. 7 (S5).

In S6, the matching determination and display control unit 35 determines whether an instruction to compare the equipment layout and the spatial layout with each other has been issued, i.e., for example, whether an instruction to perform a simulation has been issued. If there is no such instruction, the processing is finished. When there is such an instruction, the processing goes to S7. For example, when the simulation button Hb3 in the layout form P3 of FIG. 7 is pressed, the matching determination and display control unit 35 acquires spatial layout information about the expected layout space from the layout information storage unit 22 and gives advice on layout in order to place the selected medical equipment in the expected layout space. For example, the matching determination and display control unit 35 provides a simulation display. Note that instead of the simulation display, the matching determination and display control unit 35 may be set to provide a display or the like as layout advice, indicating whether a medical procedure can be performed using the selected medical equipment.

In this way, the present embodiment makes it possible to propose a candidate for medical equipment corresponding to an examination type and make proposals on selection and placement of medical equipment according to the layout and the like in a placement location where selected medical equipment is placed, and thus can effectively support preparation for medical procedures.

Note that the space information creation unit 30 can be made up, for example, of a Web service or the like. In that case, the input unit 20 may be made up of a general-purpose computer operated by the surgeon or the like, and the output unit 40 may be made up of a display or network interface configured to display output of the computer. By accessing a Web service by operating the computer, the surgeon or the like can easily grasp medical equipment that is suitable for examinations and capable of performing medical procedures in a space such as an expected room.

Second Embodiment

FIG. 11 is a block diagram showing a second embodiment. The present embodiment allows a shipment of medical equipment to be made according to an order placed by the request unit 42 shown in FIG. 1. In FIG. 11, the same components as those in FIG. 1 are denoted by the same reference signs as the corresponding components in FIG. 1, and description thereof will be omitted.

In the example of FIG. 11, the input unit 20, the space information creation unit 30, and the output unit 40 are made up of a single personal computer. By operating the input unit 20, the surgeon DO transmits order information from the request unit 42 (see FIG. 1) of the output unit 40. The order information from the request unit 42 is supplied to a communications unit 52 of a shipping device 50 through a predetermined communications channel such as the Internet.

The shipping device 50 includes an order shipping control unit 51, the communications unit 52, an inventory database (DB) 53, and a shipment instructing unit 54. The order shipping control unit 51 exerts overall control over the entire shipping device 50. The order shipping control unit 51 may be made up of a processor that uses a CPU, an FPGA, or the like. The order shipping control unit 51 may control various parts by operating according to a program stored in a non-illustrated memory or may have all or part of functions implemented using hardware-based electronic circuitry.

The inventory DB 53 communicates with the inventory management units 61 provided, respectively, in a plurality of the warehouses 60. Multiple sets of various types of medical equipment are stored in the warehouses 60. Whereas in the example of FIG. 11, three types of endoscope SC1 to SC3 differing in size are stored in one warehouse 60, not only endoscopes, but also a wide variety of medical equipment is kept in each warehouse 60. The inventory management units 61 of the respective warehouses 60 manage inventory information about inventories of medical equipment kept in the respective warehouses 60.

The inventory DB 53 acquires inventory information from the inventory management unit 61 of each warehouse 60 and stores the inventory information. The order shipping control unit 51 accesses the inventory DB 53 and thereby grasps inventory status of various types of medical equipment. Upon being given the order information received by the communications unit 52, the order shipping control unit 51 can check the inventory status of the medical equipment by accessing the inventory DB 53.

Note that before transmitting the order information, the surgeon DO may transmit inventory check information to the shipping device 50 to check the inventory by specifying medical equipment. Upon receiving the inventory check information, the order shipping control unit 51 of the shipping device 50 checks the inventory of the medical equipment specified by the inventory check information.

The order shipping control unit 51 transmits information about inventory status, i.e., the presence or absence of inventories, information about receipt/shipment date and time, and other information to the request unit 42 of the output unit 40 via the communications unit 52. The request unit 42 gives display data that is based on the information about inventory status to the display unit 41, causing the display unit 41 to display the display data. The surgeon DO may confirm the order by referring to the display of the request unit 42.

Order confirmation information is transmitted from the request unit 42 to the communications unit 52 of the shipping device 50. Upon receiving the order confirmation information, the order shipping control unit 51 gives the shipment instructing unit 54 a shipment instruction regarding the medical equipment based on the order information. Note that the order shipping control unit 51 may be set to give a shipment instruction to the shipment instructing unit 54 without informing the orderer (surgeon DO) of inventory status if inventories exist when order information is received. The shipment instructing unit 54 gives a non-illustrated distribution center or the like a shipment instruction of medical equipment specified by the order information.

Note that the request unit 42 may transmit the order information by including spatial layout information about the expected layout space in the order information. In that case, the order shipping control unit 51 may be set to give a shipment instruction after determining based on the spatial layout information whether appropriate medical equipment is ordered.

Figure 12:
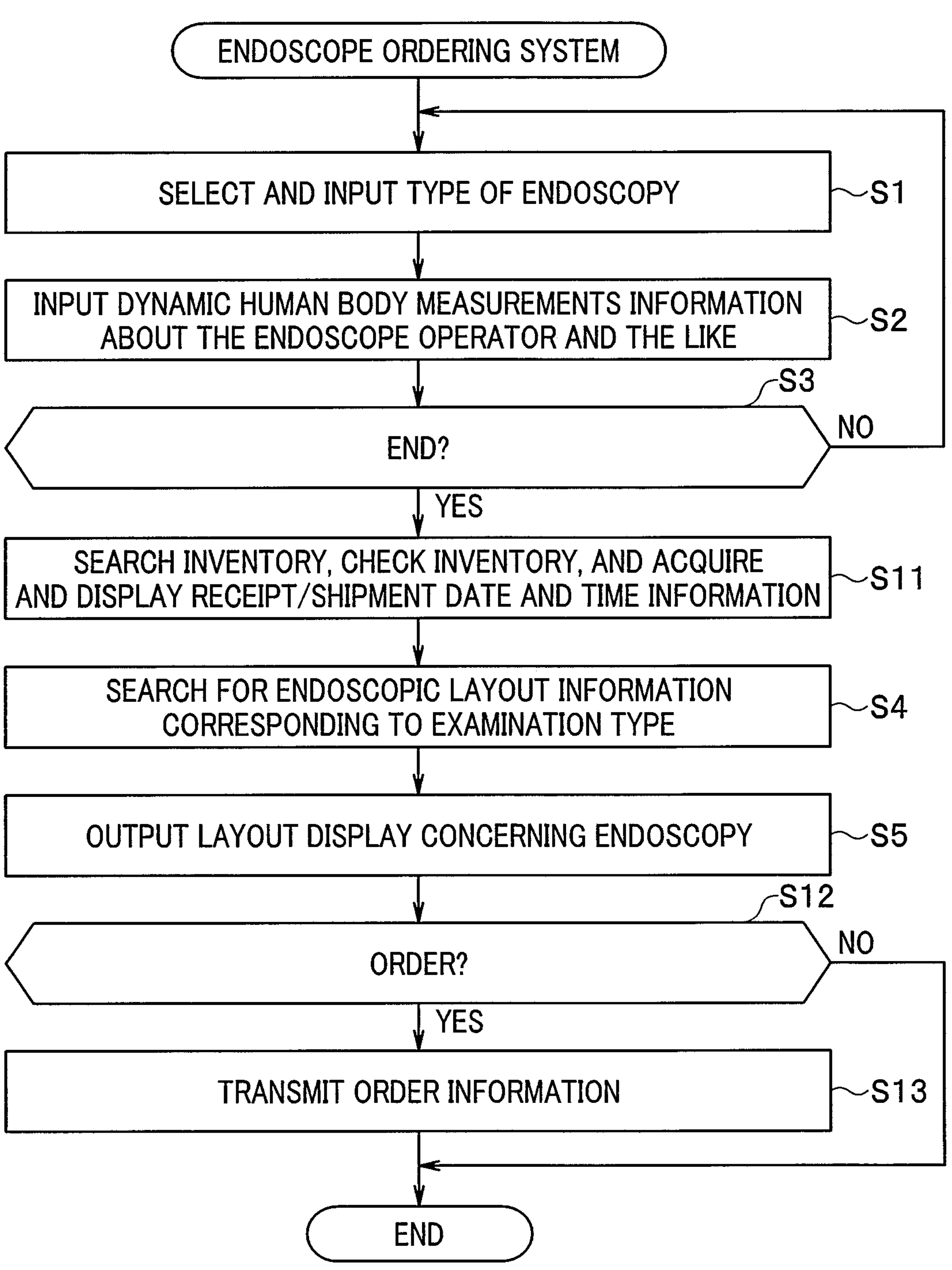
FIG. 12 is a flowchart for illustrating operation of the second embodiment.

Next, operation of the embodiment configured as described above will be described with reference to FIG. 12. FIG. 12 is a flowchart for illustrating operation of the second embodiment. In FIG. 12, the same steps as those in FIG. 10 are denoted by the same reference signs as the corresponding steps in FIG. 10, and description thereof will be omitted.

In the flowchart of FIG. 12, when the determination in step S3 is YES, the processing goes to step S11. In S11, the request unit 42 transmits inventory check information. The inventory check information is received by the communications unit 52 of the shipping device 50 and given to the order shipping control unit 51. Upon receiving the inventory check information, the order shipping control unit 51 checks the inventory of the medical equipment specified by the inventory check information.

The order shipping control unit 51 accesses the inventory DB 53, checks the inventory status of the medical equipment specified by the inventory check information, i.e., the presence or absence of an inventory, the receipt/shipment date and time, and the like, and transmits the inventory information to the request unit 42 of the output unit 40 via the communications unit 52. Consequently, the request unit 42 gives display data that is based on the information about inventory status to the display unit 41, causing the display unit 41 to display the display data.

After checking for an inventory of medical equipment corresponding to the examination type and the like, the surgeon DO causes a layout display to be presented in S4 and S5. Consequently, the surgeon DO determines whether the selected medical equipment can be used by being placed in the expected layout space. If it is determined that the medical equipment can be placed and used, the surgeon DO orders the medical equipment. The control unit 31 determines in S12 whether an order has been placed, and if an order has been placed, the control unit 31 makes the request unit 42 transmit order information (S13). Note that if it is determined that the medical equipment cannot be placed in the expected layout space, the surgeon DO finishes the process without ordering the medical equipment.

In this way, the present embodiment allows the user such as the surgeon to determine medical equipment for use to perform a medical procedure in a desired space and easily order the medical equipment.

The present disclosure is not limited to any of the precise embodiments described above, and may be embodied by changing components in the implementation stage without departing from the gist of the disclosure. Also, the disclosure can be implemented in various forms using appropriate combinations of the components disclosed in the above embodiments. For example, some of the components disclosed in the embodiments may be deleted. Furthermore, components may be combined as appropriate across different embodiments.

Of the techniques described herein, most of the control and functions described mainly in the flowchart can be set by a program, and when the program is read and executed by a computer, the control and functions described above can be implemented. Part or all of the program can be stored as a computer program product in a portable medium such as a flexible disk, a CD-ROM, or a nonvolatile memory, or a storage medium such as a hard disk or a volatile memory, and can be distributed or provided at the time of shipment or via a portable medium or a communications line. The user can easily implement the medical procedure preparation guide apparatus according to the present embodiment by installing the program on a computer by downloading via a communications network or by installing the program on a computer from a recording medium.

What is claimed is:

1. A medical procedure preparation guide apparatus comprising one or more processors comprising hardware, wherein the one or more processors being configured to:

generate a training dataset including annotated layout information of a plurality of sample endoscopes for a plurality of examination types;

train a machine learning model using the training dataset;

execute the machine learning model to create a database storing layout information in relation to a plurality of endoscopes classified by examination types;

acquire an examination type which is a type of examination or treatment using an endoscope;

search the database for layout information about a candidate endoscope corresponding to the examination type; and output the layout information about the candidate endoscope including dynamic human body measurements information about a person concerned with the examination or the treatment using the endoscope.

2. The medical procedure preparation guide apparatus according to claim 1, wherein the layout information is stored in the database by including the dynamic human body measurements information.

3. The medical procedure preparation guide apparatus according to claim 1, wherein the one or more processors being configured to output information about a result of comparison between information that indicates a spatial layout of an expected layout space in which the endoscope is placed and the layout information that includes the dynamic human body measurements information.

4. The medical procedure preparation guide apparatus according to claim 1, wherein the layout information includes information about a space for use to carry in the endoscope and a space for use to house the endoscope.

5. The medical procedure preparation guide apparatus according to claim 1, wherein dynamic human body measurements information about an operator of the endoscope is stored in the database for each of a plurality of recommended layouts of the endoscope.

6. The medical procedure preparation guide apparatus according to claim 1, wherein dynamic human body measurements information about an operator of the endoscope is corrected by inputting body size information about the operator.

7. The medical procedure preparation guide apparatus according to claim 1, wherein dynamic human body measurements information about an operator of the endoscope is corrected by inputting body size information about a target person of the examination or the treatment using the endoscope.

8. The medical procedure preparation guide apparatus according to claim 1, wherein dynamic human body measurements information about an operator of the endoscope is corrected by inputting body size information about an assistant of the examination or the treatment using the endoscope.

9. The medical procedure preparation guide apparatus according to claim 3, wherein the information that indicates the spatial layout of the expected layout space is obtained by calculating dimensions of the expected layout space and dimensions of each of members in the expected layout space based on images obtained by photographing the expected layout space.

10. The medical procedure preparation guide apparatus according to claim 3, wherein the database is created by calculating dimensions of the expected layout space and dimensions of each of members in the expected layout space based on images obtained by photographing the expected layout space in advance.

11. The medical procedure preparation guide apparatus according to claim 9, wherein the database is created by calculating dimensions of the expected layout space and dimensions of each of members in the expected layout space based on images obtained by photographing the expected layout space in advance.

12. The medical procedure preparation guide apparatus according to claim 1, wherein the medical procedure preparation guide apparatus accepts as input a photographic image taken when a specific medical endoscope is used, and outputs layout information about spaces necessary for the examination or the treatment using the endoscope, based on an inference model trained using teacher data annotated with a necessary space in using the specific endoscope.

13. The medical procedure preparation guide apparatus according to claim 1, wherein the layout information is classified into a plurality of types according to size of the endoscope.

14. The medical procedure preparation guide apparatus according to claim 1, wherein the dynamic human body measurements information is classified into a plurality of types according to dynamic human body measurements of the person concerned with the examination or the treatment using the endoscope.

15. The medical procedure preparation guide apparatus according to claim 3, wherein the spatial layout is standardized into a plurality of types.

16. A medical procedure preparation guide method, comprising:

generating a training dataset including annotated layout information of a plurality of sample endoscopes for a plurality of examination types;

training a machine learning model using the training dataset;

executing the machine learning model to create a database storing layout information in relation to a plurality of endoscopes classified by examination types;

acquiring an examination type which is a type of examination or treatment using endoscope;

searching the database for layout information about a candidate endoscope corresponding to the examination type; and outputting the layout information about the candidate endoscope including dynamic human body measurements information about a person concerned with the examination or the treatment using the endoscope.

17. A non-transitory recording medium recording a medical procedure preparation guide program, wherein the medical procedure preparation guide program causes a computer to execute procedures for:

generating a training dataset including annotated layout information of a plurality of sample endoscopes for a plurality of examination types;

training a machine learning model using the training dataset;

executing the machine learning model to create a database storing layout information in relation to a plurality of endoscopes classified by examination types;

acquiring an examination type which is a type of examination or treatment using an endoscope;

searching the database for layout information about a candidate endoscope corresponding to the examination type; and outputting the layout information about the candidate endoscope including dynamic human body measurements information about a person concerned with the examination or the treatment using the endoscope.

18. The medical procedure preparation guide apparatus according to claim 1, wherein the dynamic human body measurements information includes at least a dimension of a space necessary for a motion of a body of the person performed during the examination or the treatment.

19. The medical procedure preparation guide apparatus according to claim 18, wherein the motion of the body is twisting the body.

20. The medical procedure preparation guide apparatus according to claim 1, wherein the one or more processors is further configured to:

display, via a graphical user interface (GUI) to a user, a first image of the endoscope in superimposition on a second image of an expected layout space in which the endoscope is placed; and automatically move the first image to a position on the GUI based on an operation of the user with respect to the first image.

* * * * *